United States Patent
Govari et al.

(10) Patent No.: US 9,295,529 B2
(45) Date of Patent: Mar. 29, 2016

(54) POSITION TRACKING USING QUASI-DC MAGNETIC FIELDS

(75) Inventors: Assaf Govari, Haifa (IL); Andres Claudio Altmann, Haifa (IL); Yaron Ephrath, Haifa (IL)

(73) Assignee: Biosense Webster, Inc., Diamond Bar, CA (US)

( * ) Notice: Subject to any disclaimer, the term of this patent is extended or adjusted under 35 U.S.C. 154(b) by 1682 days.

(21) Appl. No.: 11/130,423

(22) Filed: May 16, 2005

(65) Prior Publication Data

US 2006/0293593 A1 Dec. 28, 2006

(51) Int. Cl.
*A61B 5/05* (2006.01)
*A61B 19/00* (2006.01)

(52) U.S. Cl.
CPC ............ *A61B 19/5244* (2013.01); *A61B 19/54* (2013.01); *A61B 2019/5251* (2013.01); *A61B 2019/547* (2013.01); *A61B 2019/5458* (2013.01); *A61B 2019/5475* (2013.01); *A61B 2019/5483* (2013.01)

(58) Field of Classification Search
CPC ............ A61B 5/06; A61B 2019/5251; A61B 19/5244; A61B 2019/5272; A61B 2019/5458; A61B 2019/5475; A61B 2562/0223; A61B 5/062; A61B 17/1707; A61B 2017/00725; A61B 2019/448; A61B 6/12; A61B 8/0833; A61B 19/54; A61B 2019/547
USPC .............................. 128/899; 324/309; 600/424
See application file for complete search history.

(56) References Cited

U.S. PATENT DOCUMENTS

| | | | | |
|---|---|---|---|---|
| 4,945,305 A | * | 7/1990 | Blood | 324/207.17 |
| 5,170,566 A | * | 12/1992 | Fowler et al. | 33/356 |
| 5,391,199 A | | 2/1995 | Ben-Haim | |
| 5,443,489 A | | 8/1995 | Ben-Haim | |
| 5,453,686 A | * | 9/1995 | Anderson | 324/207.17 |
| 6,073,043 A | * | 6/2000 | Schneider | 600/424 |
| 6,082,366 A | * | 7/2000 | Andra et al. | 128/899 |
| 6,172,499 B1 | * | 1/2001 | Ashe | 324/207.12 |
| 6,239,724 B1 | | 5/2001 | Doron et al. | |
| 6,371,379 B1 | * | 4/2002 | Dames et al. | 235/493 |

(Continued)

FOREIGN PATENT DOCUMENTS

| | | |
|---|---|---|
| EP | 1530057 A2 | 5/2005 |
| EP | 1530057 B1 | 5/2005 |

(Continued)

OTHER PUBLICATIONS

EP Search Report, EP Application EP 06 25 2537 dated Oct. 26, 2006.

(Continued)

*Primary Examiner* — Long V Le
*Assistant Examiner* — Ellsworth Weatherby
(74) *Attorney, Agent, or Firm* — Louis J. Capezzuto

(57) ABSTRACT

A method for tracking a position of a sensor includes generating a periodic magnetic field in a vicinity of the sensor, the field having a positive polarity phase and a negative polarity phase with respective constant positive and negative amplitudes. First and second field measurement signals are produced responsively to the magnetic field at the sensor during the positive and negative polarity phases, respectively. The position of the sensor is determined responsively to the first and second field measurement signals.

15 Claims, 3 Drawing Sheets

(56) References Cited

U.S. PATENT DOCUMENTS

| | | | |
|---|---|---|---|
| 6,427,079 B1 * | 7/2002 | Schneider et al. | 600/424 |
| 6,427,314 B1 * | 8/2002 | Acker | 29/593 |
| 6,549,004 B1 | 4/2003 | Prigge | |
| 6,618,612 B1 | 9/2003 | Acker et al. | |
| 6,690,963 B2 | 2/2004 | Ben-Haim et al. | |
| 2002/0065455 A1 | 5/2002 | Ben-Haim et al. | |
| 2003/0117270 A1 * | 6/2003 | Dimmer et al. | 340/10.1 |
| 2003/0120150 A1 | 6/2003 | Govari | |
| 2004/0068178 A1 | 4/2004 | Govari | |

FOREIGN PATENT DOCUMENTS

| | | |
|---|---|---|
| JP | 2001-500931 A | 1/2001 |
| JP | 2002-236010 A | 8/2002 |
| JP | 2006-347527 A | 12/2006 |
| WO | WO 88/02844 A1 | 4/1988 |
| WO | WO 96/05768 A1 | 2/1996 |

OTHER PUBLICATIONS

JP Office Action JP2006-135518 Dated Jul. 12, 2011.
JP Office Action JP2006-135518 Dated Dec. 13, 2011.

* cited by examiner

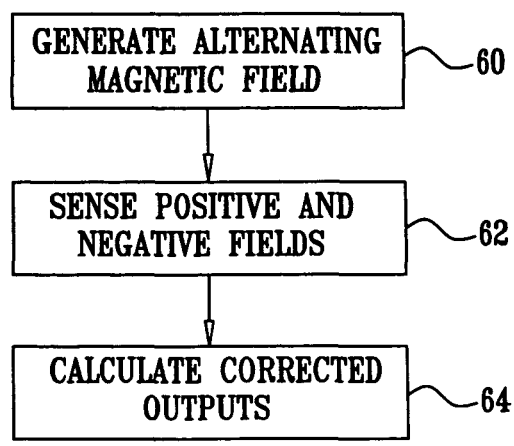

POSITION TRACKING USING QUASI-DC MAGNETIC FIELDS

FIELD OF THE INVENTION

The present invention relates generally to magnetic position tracking systems, and particularly to methods and systems for reducing measurement errors in magnetic position tracking systems.

BACKGROUND OF THE INVENTION

Various methods and systems are known in the art for tracking the coordinates of objects involved in medical procedures. Some of these systems use magnetic field measurements. For example, U.S. Pat. Nos. 5,391,199 and 5,443,489, whose disclosures are incorporated herein by reference, describe systems in which the coordinates of an intrabody probe are determined using one or more field transducers. Such systems are used for generating location information regarding a medical probe or catheter. A sensor, such as a coil, is placed in the probe and generates signals in response to externally-applied magnetic fields. The magnetic fields are generated by magnetic field transducers, such as radiator coils, fixed to an external reference frame in known, mutually-spaced locations.

Additional methods and systems that relate to magnetic position tracking are also described, for example, in PCT Patent Publication WO 96/05768, U.S. Pat. Nos. 6,690,963, 6,239,724, 6,618,612 and 6,332,089, and U.S. Patent Application Publications 2002/0065455 A1, 2003/0120150 A1 and 2004/0068178 A1, whose disclosures are all incorporated herein by reference. These publications describe methods and systems that track the position of intrabody objects such as cardiac catheters, orthopedic implants and medical tools used in different medical procedures.

Some position tracking systems, including some of the systems described in the above-mentioned references, use alternating-current (AC) magnetic fields. Other position tracking systems use direct-current (DC) fields. For example, U.S. Pat. No. 4,945,305, whose disclosure is incorporated herein by reference, describes a system for measuring the position of receiving antennae with respect to transmitting antennae, utilizing pulsed DC magnetic signals. The transmitting antennae are driven one at a time by a pulsed, direct current signal. The receiving antennae measure the transmitted magnetic fields and the earth's magnetic field. A computer converts the received signals into location and orientation outputs.

U.S. Pat. No. 5,453,686, whose disclosure is incorporated herein by reference, describes a system that generates a plurality of electromagnetic fields by applying time-division multiplexed pulsed DC signals to a plurality of field generating elements. The fields are sensed by remote sensors so as to detect the rate-of-change of each of the generated electromagnetic fields. The outputs of the remote sensors are integrated in order to establish the steady state components of the generated electromagnetic fields. The steady state components are resolved into the remote object's position and orientation.

SUMMARY OF THE INVENTION

In AC magnetic position tracking systems, the magnetic field is produced by driving field generators with alternating-current, typically sinusoidal, drive signals (hence the name "AC field"). Position tracking systems that use AC fields (referred to herein as "AC systems" for simplicity) are susceptible to measurement errors caused by metallic or other field-responsive articles located in the vicinity of the tracked object. It is well known in the art that an AC magnetic field (or any magnetic field having time-varying field strength) induces eddy currents in such articles. The eddy currents subsequently generate parasitic magnetic fields that distort the measurement of the position tracking system. Position tracking systems that use DC fields (i.e., fields that have constant field strengths over a measurement period of interest) are less sensitive to eddy current distortion.

On the other hand, position measurements based on DC fields are often less stable, because the measurements are subject to baseline drift, as will be explained below. Furthermore, DC systems inevitably incorporate the earth's magnetic field into their measurements, which constitutes an additional error factor in the position measurement. Pulsed DC fields permit the effect of the earth's magnetic field to be subtracted out of the measurement, but still require a separate calibration procedure to adjust for the baseline drift.

Embodiments of the present invention provide improved methods and systems for tracking the position and orientation of an object using a "quasi-DC" magnetic field. The disclosed methods and systems provide the eddy current immunity characteristic of DC systems, while providing the ability to compensate for bias drift and for the earth's magnetic field.

In some embodiments, a quasi-DC field is generated by a periodic drive signal that has the form of a square wave. The drive signal (and the corresponding magnetic field) alternates between two phases having positive and negative polarities. During each phase, the magnetic field can be regarded as a DC field, eliminating the effects of eddy currents. The position and orientation tracking system combines measurements taken during the two phases to cancel out bias drift and measurement errors due to the earth's magnetic field.

There is therefore provided, in accordance with an embodiment of the present invention, a method for tracking a position of a sensor, including:

generating a periodic magnetic field in a vicinity of the sensor, the field having a positive polarity phase and a negative polarity phase with respective constant positive and negative amplitudes;

producing first and second field measurement signals responsively to the magnetic field at the sensor during the positive and negative polarity phases, respectively; and determining the position of the sensor responsively to the first and second field measurement signals.

In an embodiment, the sensor is implanted in a body of a patient. Additionally or alternatively, the sensor is coupled to a medical instrument that is used to treat a patient.

In another embodiment, each of the positive and negative polarity phases is constant for a duration of at least 10 milliseconds. In yet another embodiment, the positive amplitude is equal to the negative amplitude.

In still another embodiment, determining the position of the sensor includes performing an arithmetic operation on the first and second field measurement signals. In another embodiment, performing the arithmetic operation includes summing the first and second field measurement signals to produce a position signal.

In an embodiment, the first and second field measurement signals include transient intervals, and producing the first and second field measurement signals includes measuring the signals outside the transient intervals.

In another embodiment, generating the periodic magnetic field includes multiplexing two or more periodic magnetic fields generated at two or more different, respective locations.

There is additionally provided, in accordance with an embodiment of the present invention, a method for tracking a position of a position transducer, including:

operating the position transducer to generate a periodic magnetic field having a positive polarity phase and a negative polarity phase with respective constant positive and negative amplitudes;

sensing the magnetic field at a known location so as to produce, responsively to the sensed magnetic field, first and second field measurement signals during the positive and negative polarity phases, respectively; and determining the position of the position transducer responsively to the first and second field measurement signals.

There is also provided, in accordance with an embodiment of the present invention, apparatus for tracking a position of an object, including:

at least one location pad, which is arranged to generate a periodic magnetic field in a vicinity of the sensor, the field having a positive polarity phase and a negative polarity phase with respective constant positive and negative amplitudes;

a position sensor, which is coupled to the object and is arranged to produce first and second field measurement signals responsively to the magnetic field during the positive and negative polarity phases, respectively; and a processor, which is arranged to determine the position of the sensor responsively to the first and second field measurement signals.

There is further provided, in accordance with an embodiment of the present invention, apparatus for tracking a position of an object, including:

a field generator, which is coupled to the object and is arranged to generate a periodic magnetic field having a positive polarity phase and a negative polarity phase with respective constant positive and negative amplitudes;

a location pad, which is arranged to produce first and second field measurement signals responsively to the magnetic field during the positive and negative polarity phases, respectively; and a processor, which is arranged to determine the position of the sensor responsively to the first and second field measurement signals.

The present invention will be more fully understood from the following detailed description of the embodiments thereof, taken together with the drawings in which:

BRIEF DESCRIPTION OF THE DRAWINGS

FIG. 4 is a flow chart that schematically illustrates a method for position tracking, in accordance with an embodiment of the present invention.

DETAILED DESCRIPTION OF EMBODIMENTS

System Description

Figure 1:
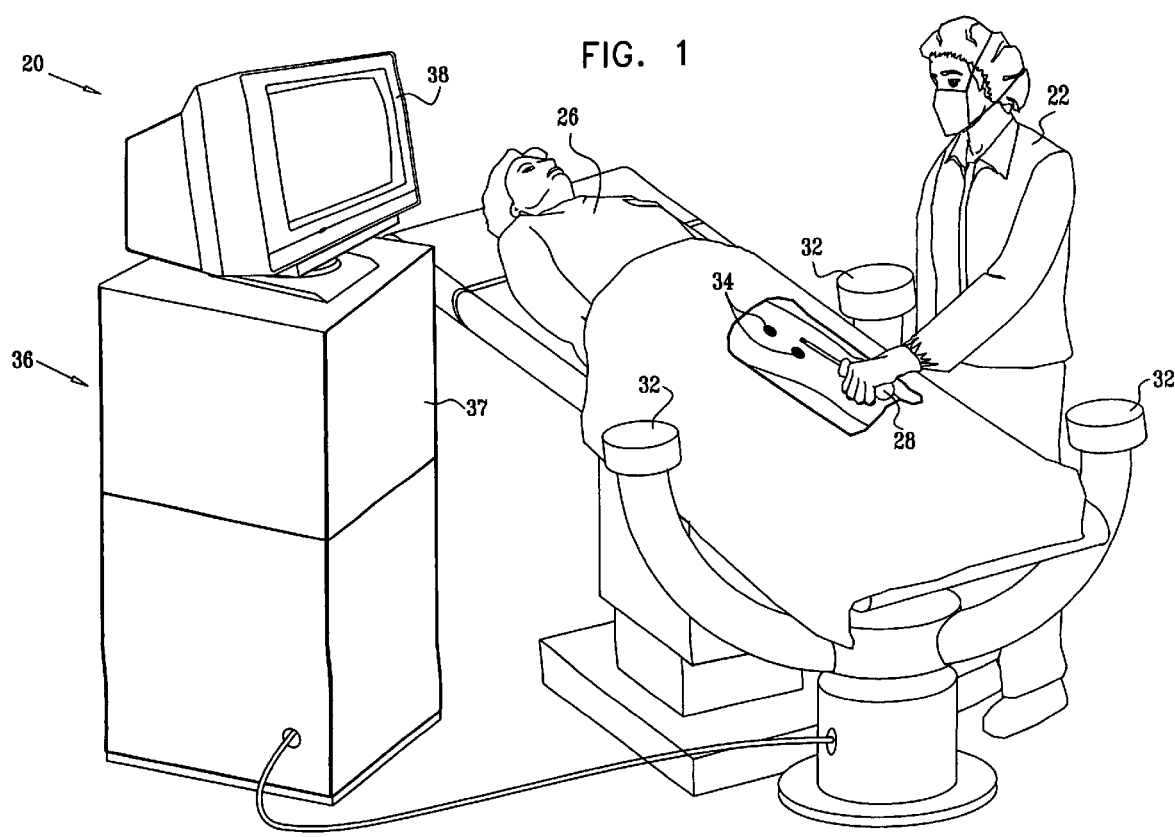
FIG. 1 is a schematic, pictorial illustration of a magnetic position tracking system, in accordance with an embodiment of the present invention.

FIG. 1 is a schematic, pictorial illustration of a magnetic position and orientation tracking system 20, in accordance with an embodiment of the present invention. A surgeon 22 performs a medical procedure on a patient 26 using a medical tool 28. The tracking system that guides the surgeon comprises location pads 32, which function as field generators. The location pads typically comprise field generating coils, which generate quasi-DC magnetic fields throughout a predetermined working volume that comprises the surgical site. The fields are generated in response to drive signals generated by a console 36. The magnetic fields are sensed by miniature sensor units 34 introduced into the patient's body, as will be described in detail below. In the example shown in FIG. 1, the sensor units are implanted in the patient's leg.

Each sensor unit comprises position sensors that are designed to sense the magnetic field in their vicinity. The magnetic fields generated by location pads 32 cause sensor units 34 to generate and transmit position signals that are indicative of the position and orientation of the sensor unit. The position signals are received by a wireless control unit, which is coupled to a computer 37, both located in console 36. Computer 37, which serves as the central processor of system 20, processes the received signals in order to calculate the relative location and orientation coordinates of sensor units 34. The results are typically presented to the surgeon on a display 38. (In the context of the present patent application and in the claims, the terms "position" and "position coordinates" refer to both location and orientation of the sensor unit. Typically, positions are represented in terms of six-dimensional coordinates.)

The tracking system guides the surgeon in performing the procedure, in this example a knee-joint operation, by measuring and presenting the positions and orientation of sensor units 34. In some applications, a unit similar to sensor units 34 is also fitted into tool 28. In such application, the tracking system may measure and present the position of the tool in respect to the intrabody sensor units.

The system shown in FIG. 1 is related to an orthopedic application. Further details regarding position tracking systems for orthopedic applications can be found in U.S. Provisional Patent Application No. 60/550,924, filed Mar. 5, 2004, now filed as U.S. patent application Ser. No. 11/062,258, which is assigned to the assignee of the present patent application and whose disclosure is incorporated herein by reference. However, this exemplary system was chosen purely for the sake of conceptual clarity. Other system configurations and other applications will be apparent to those skilled in the art and are considered to be within the scope of the present invention. For example, any number of sensor units 34 and location pads 32 can be used. Sensor units can be fitted into other types of implants and medical tools, as well as into invasive medical instruments such as catheters and endoscopes. The location pads may alternatively be attached to the patient's body.

Location pads 32 and sensor units 34 can be designed to either transmit or receive magnetic fields. In other words, if sensor unit 34 is configured to receive magnetic fields, then location pads 32 are configured to generate fields. Alternatively, the location pads may be configured to sense fields generated by field generators fitted into the implants and/or the tool. In the description that follows it is assumed that location pads 32 generate the magnetic fields, which are received by sensor units 34 in the implants and in tool 28. In configurations in which the roles of transmitter and receiver are reversed, the principles of the present invention can be used to measure the positions of sensor units 34 by driving field transducers in the sensor units to generate quasi-DC fields, and sensing the fields at the location pads.

Figure 2:
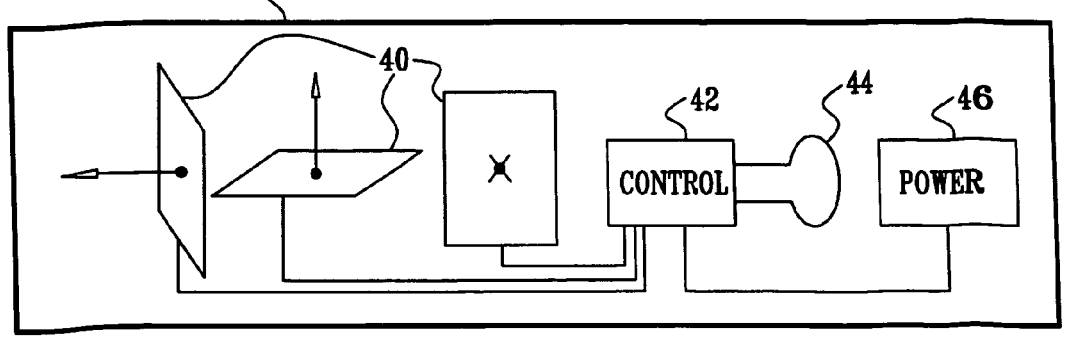
FIG. 2 is a block diagram that schematically illustrates a sensor unit, in accordance with an embodiment of the present invention.

FIG. 2 is a block diagram that schematically shows details of sensor unit 34, in accordance with an embodiment of the present invention. Sensor unit 34 comprises position sensors 40, which are designed to sense and measure the magnetic field in their vicinity. The sensor unit typically comprises three position sensors 40 mounted in mutually-orthogonal orientations. Each sensor 40 measures a component of the magnetic field, according to the orientation of the sensor. The magnetic field detected during each phase of the quasi-DC field is substantially a DC field. Therefore, position sensors 40 are designed to sense DC magnetic fields. In one embodiment, sensors 40 comprise magneto-resistive transducers that change their electrical conductivity proportionally to the sensed magnetic field. Alternatively, sensors 40 may comprise Hall-effect transducers that produce a voltage proportional to the sensed magnetic field. Further alternatively, any other sensor that is suitable for measuring DC magnetic fields can be used for implementing position sensors 40.

Position sensors 40 sense the components of the magnetic field and produce voltages that are processed by control circuitry 42. Circuitry 42 produces position signals responsively to the voltages and transmits the signals to the wireless control unit in console 36 using a transmission coil 44. A power unit 46 provides electrical power for operating control circuitry 42. In some embodiments, power unit 46 comprises a battery. In other embodiments, power unit 46 comprises a power coil, which receives radio frequency (RF) energy transmitted to the sensor unit from the external system. In these embodiments, the power unit rectifies the received RF signal and uses the resulting DC voltage for powering circuitry 42.

In some embodiments, sensor unit 34 is connected by wires to console 36. For example, sensor unit 34 can be fitted in the distal end of a catheter or a similar invasive instrument. The catheter comprises wires that connect its distal end with the external system. In such embodiments, transmission coil 44 can be omitted and the position signals sent to the external system using the wired connection. Additionally or alternatively, power unit 46 may similarly be omitted, and power supplied to the control circuitry via the wired connection.

Figure 3A:
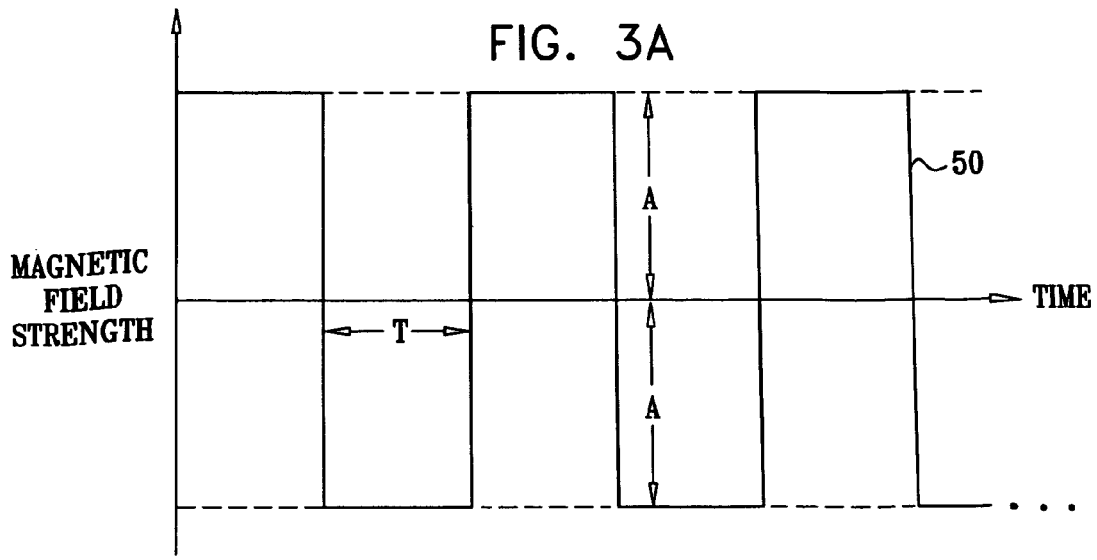
FIG. 3A is a signal diagram that schematically illustrates a magnetic field strength, in accordance with an embodiment of the present invention.

FIG. 3A is a signal diagram that schematically illustrates a magnetic field strength of a quasi-DC magnetic field, in accordance with an embodiment of the present invention. A curve 50 shows the field strength of the magnetic field generated by one of location pads 32 responsively to a quasi-DC drive signal. The generated field (also referred to as the "primary field") has the form of a symmetrical square wave. In this embodiment, the field comprises positive and negative polarity phases, both having equal absolute magnitudes (denoted A in the figure). Each polarity phase has a duration denoted T. The frequency of the drive signal and of the field is thus defined as $f=\frac{1}{2}T$. Although in the exemplary embodiment of FIG. 3A the negative and positive polarities of the primary field are shown as having equal magnitudes and equal time durations, in other embodiments the negative and positive polarities may be unequal. Similarly, the time durations of the positive and negative polarity phases need not be equal.

Figure 3B:
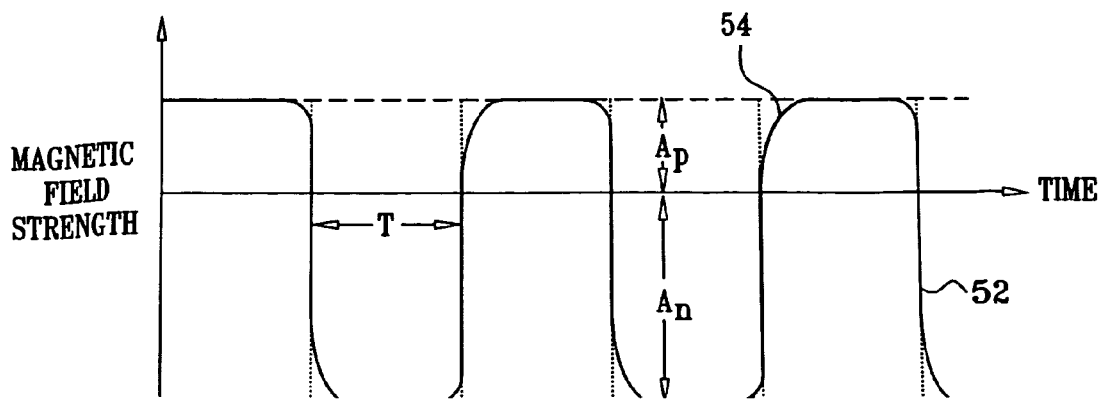
FIG. 3B is a signal diagram that schematically illustrates a detected magnetic field, in accordance with an embodiment of the present invention.

FIG. 3B is a signal diagram that schematically illustrates a detected quasi-DC magnetic field, in accordance with an embodiment of the present invention. A curve 52 shows a typical signal magnitude of a signal produced by one of position sensors 40 in one of sensor units 34, responsively to the field shown by curve 50. As shown by curve 52, the signal is not symmetrical. In the example illustrated by curve 52, the absolute magnitude of the negative phase (denoted $A_n$ in the figure) is larger than the absolute magnitude of the positive phase (denoted $A_p$).

The asymmetry of the sensed quasi-DC field is caused mainly by two factors, namely baseline drift and the Earth's magnetic field. Baseline drift is a term referring to slow temporal variations in the field-strength measurement. Such variations can be caused, for example, by temperature variations and component value drift in the electronic circuitry used to amplify, filter and sample the measured signals in the sensor unit and in the external system.

Baseline drift can be represented by an equivalent magnetic field vector that is vector-added to the primary magnetic field vector in the vicinity of the position sensor. Since each position sensor 40 detects a component of this composite field, the bias drift vector will decrease the value of one polarity phase of the detected field and increase the value of the opposite polarity by the same amount. The result of this effect is an asymmetry, or an offset, in the magnitudes of the positive and negative polarity phases, as shown in curve 52.

Measurement of the quasi-DC primary field combined with the Earth's magnetic field causes a similar asymmetry effect. One polarity phase of the detected quasi-DC field is increased by the contribution of the Earth's magnetic field, while the opposite polarity phase is decreased by the same amount. In both cases, the error can be determined by subtracting the values of the positive and negative polarity phases of the detected field. A corrected field estimate can be produced by calculating the average between the sensed positive and negative polarity phases. Following the notation of FIGS. 3A and 3B, the error is given by $\epsilon=(A_p-A_n)/2$. The corrected field estimate is given by $A=A_p-\epsilon$ or $A=A_n+\epsilon$, or directly by $A=(A_p+A_n)/2$. (All calculations assume that $A_p$ and $A_n$ are positive numbers, representing the absolute values of the sensed field strengths.) The position tracking method described in FIG. 4 below uses such measurements, taken during the two polarity phases of the quasi-DC field, to compensate for bias drift and errors due to the Earth's magnetic field.

In some embodiments, the opposite polarity measurements of the quasi-DC field can also be used to simplify the calibration of the sensor unit. In some cases the calibration can be eliminated completely.

In addition to the asymmetry effect, the sensed field shown in curve 52 comprises transients 54 around the transitions between positive and negative polarities. The transients deviate from the well-defined, square-wave shape of the primary field shown in curve 50. Transients 54 are caused, for example, by eddy currents or other sources of parasitic fields that are excited by variations in the primary field, rather than by the field itself. (These parasitic effects are one of the major error contributors in positioning systems based on AC fields.) When sensing the magnetic field in the disclosed quasi-DC system using sensors 40, the transients are avoided by performing the measurement after the transients decay and the field strength has stabilized. Under these measurement conditions, the sensed field can be safely regarded as a DC field.

The frequency of the quasi-DC field is also chosen with respect to transient responses such as transients 54. As explained above, it is desirable to regard the magnetic field in each polarity phase as a DC field. In order to do so, each of the positive and negative polarity phases of the quasi-DC field should remain constant for a sufficiently long interval, T, to allow parasitic effects such as eddy currents to decay before sensing the field. T values of 10 milliseconds or more (corresponding to square wave frequencies of 50 Hz or less) are typically considered sufficient for quasi-DC operation, although other ranges can also be used.

Another factor that affects the choice of quasi-DC field frequency is the desired measurement refresh rate (i.e., the number of position measurements per unit time). The refresh rate is typically determined based on the expected dynamics of the sensor unit and the desired measurement accuracy and resolution.

Position Sensing Method

FIG. 4 is a flow chart that schematically illustrates a method for position tracking, in accordance with an embodiment of the present invention. The method description below considers a single location pad 32 and a single sensor unit 34 for the sake of simplicity. The generalized case of a system comprising several location pads and several sensor units is described afterwards.

The method begins with the position tracking system generating a quasi-DC magnetic field, at a field generation step 60. Console 36 generates a quasi-DC drive signal that is used to drive location pad 32, so as to generate a quasi-DC magnetic field throughout the working volume.

The quasi-DC field generated by the location pad is sensed by position sensors 40 of sensor unit 34, at a field sensing step 62. Control circuitry 42 detects the voltages or currents corresponding to the positive and negative polarity phases of the sensed fields. (The detected voltages or currents correspond to field strengths $A_p$ and $A_n$ in curve 52 of FIG. 3B above.)

The control circuitry produces field measurement signals, corresponding to the measured values of $A_p$ and $A_n$ and produces a corrected field estimate, at an output calculation step 64. In one embodiment, the control unit then produces position signals indicative of the corrected field estimate and sends the position signals to computer 37, as described above. In one embodiment, the control circuitry comprises a filter that calculates the corrected field estimate using the relation $A=(A_p+A_n)/2$ given above. In an alternative embodiment, the field measurement signals indicative of the values of $A_p$ and $A_n$ are sent by the control circuitry to computer 37, and the calculation of the corrected field estimate and the position signals is carried out by the computer. Alternatively, any other suitable method for calculating the corrected field estimate using the measured values of $A_p$ and $A_n$ can be used. Such methods may comprise either software or hardware implementations. The corrected field estimate is then used by computer 37 to calculate the position coordinates of sensor unit 34.

In many practical cases, system 20 comprises several location pads 32. In such embodiments, each location pad 32 generates its quasi-DC field separately, while the other location pads do not generate any magnetic field. Any suitable time-division-multiplexing (TDM) allocation between the different location pads can be used to fulfill this condition. It is desirable, however, that the positive and negative polarity phases generated by a given location pad be temporally adjacent to one another. The adjacency ensures that the primary field will be similar in both phases, and that the bias drift will remain approximately constant. In one embodiment, steps 60-64 are repeated for each location pad 32, in accordance with a predetermined (TDM) sequence. Computer 37 receives multiple position signals from the sensor unit in response to the sensed field of each location pad. The computer uses the position signals to calculate the position coordinates of the sensor unit using methods of position calculation known in the art.

The methods described above can be used without change in systems comprising multiple sensor units 34, since each sensor unit performs its measurements independently of other sensor units.

Although the methods and systems described herein mainly address the use of quasi-DC magnetic fields in medical position tracking systems, the principles of the present invention can also be used in non-medical position tracking systems, as well as in other applications. It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art.

The invention claimed is:

1. A method for tracking a position and orientation of a sensor unit on a medical tool during a medical procedure, comprising:
    driving a plurality of field generators in the vicinity of the sensor unit to generate a periodic quasi-DC magnetic field using a square wave drive signal, the magnetic field having the form of a symmetric square waveform with a positive polarity phase and a negative polarity phase;
    producing first and second field measurement signals responsively to the magnetic field during the positive and negative polarity phases, respectively, using at least one position sensor provided within the sensor unit;
    determining a corrected field estimate from the first and second field measurement signals from the positive and negative polarity phases for correcting a baseline drift caused by sources of parasitic fields by ensuring each of the positive and negative polarity phases has a constant period for a duration of at least 10 milliseconds;
    determining six-dimensional coordinates of the sensor unit position responsive to the first and second field measurement signals using the corrected field estimate; and
    displaying the position of the sensor unit on a display.

2. The method according to claim 1, wherein the sensor unit is implanted in a body of a patient.

3. The method according to claim 1, wherein the medical tool is used to treat a patient that is used to treat a patient.

4. The method according to claim 1, wherein determining the position of the sensor comprises performing an arithmetic operation on the first and second field measurement signals.

5. The method according to claim 4, wherein performing the arithmetic operation comprises summing the first and second field measurement signals to produce a position signal.

6. The method according to claim 1, wherein the first and second field measurement signals comprise a steady-state portion and a transient portion, and wherein producing the first and second field measurement signals comprises measuring during the steady-state portion of the signals.

7. The method according to claim 1, wherein generating the periodic magnetic field comprises multiplexing two or more periodic magnetic fields generated at two or more different, respective locations.

8. A method of tracking a position of a sensor unit on a medical tool during a medical procedure, comprising:
    driving at least one field generator within the sensor unit to generate a periodic quasi-DC magnetic field using field using a square wave drive signal, the magnetic field having the form of a symmetric square waveform with a positive a polarity phase and a negative polarity phase;

producing first and second field measurement signals responsive to the magnetic field during the positive and negative polarity phases, respectively, using at least one location pad provided in the vicinity of the sensor unit;

determining a corrected field estimate from the first and the second field measurement signals from the positive and negative polarity phases for correcting a baseline drift caused by sources of parasitic fields by ensuring each of the positive and negative polarity phases has a constant period for a duration of at least 10 milliseconds;

determining six dimensional coordinates of the sensor unit position responsive to the first and second field measurement signals using the corrected field estimate; and displaying the position of the sensor unit on a display.

9. An apparatus for tracking a position of a medical tool during a medical procedure, comprising:

a sensor unit comprising at least one position sensor, the sensor unit being coupled to the medical tool;

a plurality of field generators configured to receive a square wave drive signal from a console that causes the field generators to generate a periodic quasi-DC magnetic field in the vicinity of the sensor unit, the field having the form of symmetric square waveform with a positive polarity phase and a negative polarity phase, each phase having a constant period for a duration of at least 10 milliseconds;

the at least one position sensors being configured to produce first and second field measurement signals responsive to the positive and negative polarity phases, respectively;

a processor configured to determine a corrected field estimate from the first and the second field measurement signals for correcting a baseline drift caused by sources of parasitic fields by using the measurements taken during the constant period duration positive and negative polarity phases, the processor further configured to determine six-dimensional coordinated of the sensor unit position using the corrected field estimate; and a display configured to display the sensor unit positon.

10. The apparatus according to claim 9, wherein the sensor unit is configured to be implantable in a body of a patient.

11. The apparatus according to claim 9, wherein the processor is adapted to determine the position of the sensor by performing an arithmetic operation on the first and second field measurement signals.

12. The apparatus according to claim 11, wherein the arithmetic operation comprises summation the first and second field measurement signals to produce a position signal.

13. The apparatus according to claim 9, wherein the first and second field measurement signals comprise a steady-state portion and a transient portion, and wherein the processor is adapted to measure the field measurement signals during the steady-state portion of the signals.

14. The apparatus according to claim 9, wherein the plurality of field generators are positioned at two or more different, respective locations, which are multiplexed to generate two or more periodic magnetic fields.

15. An apparatus for tracking a position of a medical tool having a sensor unit, the apparatus comprising:

at least one field generator provided within the sensor unit and configured to receive a square wave drive signal from a console that causes the field generators to generate a periodic quasi-DC magnetic field, the field having the form of a symmetric square waveform with a positive polarity phase and a negative polarity phase, each phase having a constant period for a duration of at least 10 milliseconds;

at least one location pad arranged in the vicinity of the sensor unit and configured to produce first and second field measurement signals responsive to the positive and negative polarity phases, respectively;

a processor configured to determine a corrected field estimate from the first and the second field measurement signals for correcting a baseline drift caused by sources of parasitic fields by using the measurements taken during the constant period duration positive and negative polarity phases, the processor further configured to determine six-dimensional coordinates of the sensor unit position using the corrected field estimate; and a display configured to display the sensor unit position.

* * * * *